United States Patent [19]

Law et al.

[11] Patent Number: 5,110,932

[45] Date of Patent: * May 5, 1992

[54] POLYSUBSTITUTED ARYL ACRIDINIUM ESTERS

[75] Inventors: Say-Jong Law, Westwood; Steve C. S. Chang, Franklin; Stephen A. Palmacci, Walpole; Roger S. Cubicciotti, Needham, all of Mass.

[73] Assignee: Ciba Corning Diagnostics Corp., Medfield, Mass.

[*] Notice: The portion of the term of this patent subsequent to Apr. 17, 2007 has been disclaimed.

[21] Appl. No.: 478,819

[22] Filed: Mar. 1, 1990

Related U.S. Application Data

[60] Continuation of Ser. No. 133,792, Dec. 14, 1987, Pat. No. 4,918,192, which is a division of Ser. No. 915,527, Oct. 6, 1986, Pat. No. 4,745,181.

[51] Int. Cl.⁵ .......................................... C07D 219/04
[52] U.S. Cl. ................................. 546/102; 546/104; 546/107
[58] Field of Search ...................... 546/102, 104, 107

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 530/387 |
| 4,918,192 | 4/1990 | Law et al. | 546/104 |
| 4,946,958 | 8/1990 | Campbell et al. | 546/104 |
| 4,950,613 | 8/1990 | Arnold, Jr. et al. | 436/546 |

FOREIGN PATENT DOCUMENTS

| | | | |
|---|---|---|---|
| 0216553 | 4/1987 | European Pat. Off. | 546/102 |
| 0324202 | 7/1989 | European Pat. Off. | 546/102 |
| 0330050 | 8/1989 | European Pat. Off. | 546/104 |
| 0361817 | 4/1990 | European Pat. Off. | 546/102 |
| 1461877 | 1/1977 | United Kingdom | 546/102 |

OTHER PUBLICATIONS

McCapra, et al., Chemical Abstracts, vol. 112(23): 213573g (1989).

*Primary Examiner*—Diana G. Rivers
*Attorney, Agent, or Firm*—Arthur S. Morgenstern; Nicholas I. Slepchuk, Jr.

[57] ABSTRACT

The present invention relates to novel acridinium esters which are useful as luminescent labels in specific binding assays such as immunoassays or nucleic acid hybridization assays. More particularly, polysubstituted aryl acridinium esters are highly stable labels for use in a chemiluminescent immunoassay.

6 Claims, No Drawings

POLYSUBSTITUTED ARYL ACRIDINIUM ESTERS

This is a continuation of application Ser. No. 133,792, filed Dec. 14, 1987, now issued as U.S. Pat. No. 4,918,192, which is a division of application Ser. No. 915,527, filed Oct. 6, 1986, now U.S. Pat. No. 4,745,181.

TECHNICAL FIELD

The present invention relates to novel acridinium esters which are useful as luminescent labels in specific binding assays such as immunoassays or nucleic acid hybridization assays. More particularly, polysubstituted aryl acridinium esters have been found to be unexpectedly stable labels for use in a chemiluminescent immune assay.

BACKGROUND ART

The use of unsubstituted aryl acridinium esters as chemiluminescent labels is disclosed by J. S. Woodhead et al first in GB 2, 008, 247 B, and again in European Patent Application No. EP 82,636. However, these compounds did not have any substituents on the ortho positions of the phenoxy ring which constitutes part of the aryl ester component. Unfortunately the Woodhead compounds were not stable in pH 7.4 buffer media, and thus, not useful for commercial assays.

DISCLOSURE OF THE INVENTION

The present invention comprises novel polysubstituted aryl acridinium esters and luminescent labelled conjugates using these esters. As a result of these substitutions, the present compounds and conjugates have an unexpectedly better stability in pH 7.4 buffer media, a threefold increase in light emitting efficiency when configured as a conjugate, and a twofold improvement in the signal-to-noise ratio when used in a solid phase specific binding assay.

More particularly, the following compounds are representative of the present invention. A luminescent compound comprising a polysubstituted aryl acridinium ester selected from the group having the following structure:

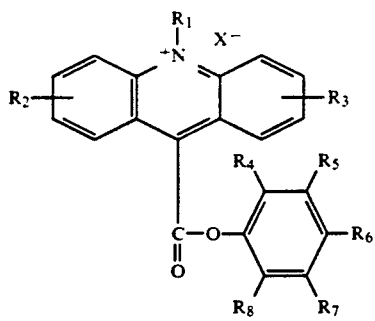

where $R_1$ is an alkyl, alkenyl, alkynyl, or aryl group; $R_2$, $R_3$, $R_5$, or $R_7$ are a hydrogen, amino, carboxyl, hydroxyl, alkoxyl, nitro, or halide group; $R_4$ or $R_8$ are an alkyl, alkenyl, alkynyl, aryl, alkoxyl, amino, amido, sulfonamido, or sulfide group; $R_6$ is a hydrogen, amino, carboxyl, hydroxyl, alkoxyl, nitro, or halide; or $R_6$ represents the following substituent:

where $R_9$ is not required but optionally can be an alkyl, aryl, or aralkyl group, and $R_{10}$ is selected from the following:

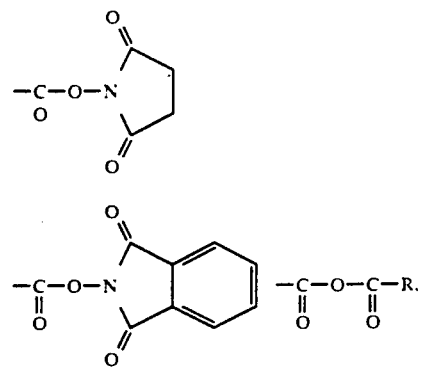

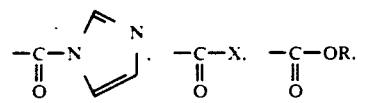

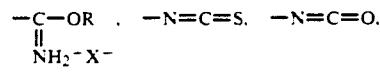

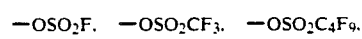

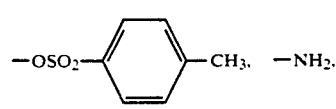

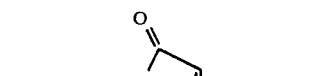

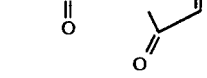

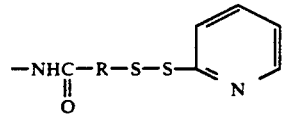

X is $CH_3SO_4^-$, $OSO_2F^-$, a halide, $OSO_2CF_3^-$, $OSO_2C_4F_9^-$,

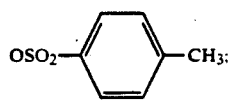

and R is alkyl, aryl, aralkyl group; and finally $R_5$, $R_6$, and $R_7$ substituent positions on the phenoxy ring are interchangeable.

Other luminescent compounds within the scope of the present invention comprise polysubstituted aryl acridinium esters selected from the group having the following structure:

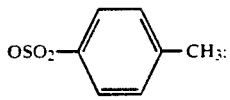

where $R_1$ is an alkyl, alkenyl, alkynyl, or aryl group; $R_2$, $R_3$, $R_5$, $R_6$ or $R_7$ are a hydrogen, amino, carboxyl, hydroxyl, alkoxyl, nitro, or halide group; $R_4$ or $R_8$ are an alkyl, alkenyl, alkynyl, aryl, alkoxyl, amino, amido, sulfonamido, or sulfide group; and finally $R_5$, $R_6$ and $R_7$ substituent positions on the phenoxy ring are interchangeable Applicants believe that the remarkable improvements in the performance of the present polysubstituted aryl acridinium esters over the prior unsubstituted ones as labels for specific binding assays arises from the shielding of the aryl ester linkage in the present compounds. Steric effects, electronic effects, or a combination thereof enable these compounds to be commercially useful in luminescent assays using specific binding phenomena known to the art such as antibody/antigen immunological reactions or complementary nucleic acid hybridization reactions.

As known in the art, labelling compounds for these assays can be used in many different conventional architectures including being coupled either to the ligand or analyte (such as an antigen), or to the specific binding partner of the ligand or analyte (such as the corresponding antibody).

Modes of the Invention

Preferentially, the present polysubstituted aryl acridinium ester compounds should be as described above with the following substituents: $R_1$ is a methyl group; $R_2$, $R_3$, $R_5$, and $R_7$ are hydrogen; $R_4$ and $R_8$ are a methyl or methoxyl group, $R_{10}$ is an N-succinimidyl oxycarbonyl group attached directly to the para-position of the phenoxy ring, and X is $CH_3SO_4^-$. In an additional embodiment, the present polysubstituted aryl acridinium ester compounds should be as described above with the following substituents: $R_1$ is a methyl group; $R_2$, $R_3$, $R_5$, $R_6$ and $R_7$ are hydrogen; $R_4$ and $R_8$ are a methyl or a methoxyl group; and X is $CH_3SO_4^-$. The following Examples disclose how to synthesize a preferred compound, the ortho-dimethyl aryl acridinium ester. In an additional preferred embodiment, the present polysubstituted aryl acridinium ester compounds should be as described above with the following substituents: $R_1$ is a methyl group; $R_2$, $R_3$, $R_5$, $R_6$ and $R_7$ are hydrogen; $R_4$ and $R_8$ are a methyl group; and X is $CH_3SO_4^-$.

Synthesis of Preferred Compounds

EXAMPLE 1

Preparation of the Potassium Salt of 3,5-Dimethyl-4-Hydroxybenzoic Acid

To a solution of 3,5-dimethyl-4-hydroxybenzoic acid (7.8 g, 47 mmole) in 50 ml of methanol was added dropwise 2.5 N NaOH until the pH of the mixture was about 7.0. The reaction mixture was stirred at room temperature for one hour and evaporated to dryness under a vacuum. The residue was triturated with acetone and filtered. The desired potassium salt was collected as a white salt then washed with acetone, and air dried (7.6 g, 80%).

EXAMPLE 2

Preparation of the Benzyl Ester of 3,5-Dimethyl-4-Hydroxybenzoic Acid

The potassium salt of 3,5-dimethyl-4-hydroxybenzoic acid in Example 1 (5.6 g, 27 mmole), dibenzo-18-crown-6 (1.0 g, 3 mmole) and 100 ml of DMF/acetonitrile (1:2, v/v) were added to a 250 ml round bottom flask equipped with a reflux condenser, a drying tube, and a stirring bar. The mixture was heated in an oil bath at 80° C. for 30 min, before adding benzyl chloride (3.5 ml, 30 mmole). This reaction mixture was heated at 80° C. for another 3 hours, cooled and filtered. The filtrate was evaporated to dryness. The residue was taken up with a minimal amount of chloroform and purified on a packed silica gel column (60 A, 230-400 mesh) which was eluted with chloroform/hexane (3:1, v/v). The elution was later changed to 100% chloroform. The fractions having an Rf of 0.6 on E. Merck silica gel TLC plate when developed with toluene/ethyl acetate (4:1, v/v) were pooled, then evaporated to give a white solid, the desired benzyl ester (4.8 g, 70%, m.p. 108° C.).

EXAMPLE 3

Preparation of 9-Acridinecarbonyl Chloride

A mixture of 9-acridinecarboxylic acid hydrate (7.3 g, 30 mmole), and thionyl chloride (50 ml, 0.685 mole) was heated at reflux in a round bottom flask equipped with a reflux condenser, a drying tube, and a stirring bar. The reaction mixture was heated further for one hour after the dissolution occurred, the cooled and evaporated to remove any excess thionyl chloride. The residue was directly utilized in the subsequent reaction without further purification.

EXAMPLE 4

Preparation of 2',6'-Dimethyl-4'-Benzyloxycarbonylphenyl Acridine-9-Carboxylate

A solution of the benzyl ester of 3,5-dimethyl-4-hydroxybenzoic acid from Example 2 (6.4 g, 25 mmole) and 4-dimethylaminopyridine (345 mg, 3 mmole) in 50 ml of pyridine (over 3 A molecular sieves) was heated at 90° C. in a round bottom flask equipped with a drying tube. The solution was cooled and pipetted into a flask containing the dried acridine-9-carbonyl chloride from Example 3 (7.05 g, 29.2 mmole). The reaction mixture was stirred at 100° C. for 3 hours, then at room temperature overnight. After the removal of solvent, the crude product was purified on a packed silica gel column which was eluted with chloroform, followed by elution with ethylacetate. The desired product having an Rf of 0.6 in toluene/ethylacetate (4:1, v/v) was further purified by crystallization from ethylacetate/hexane (6.37 g, 50%; m.p. 146°-148° C.).

EXAMPLE 5

Preparation of 2',6'-Dimethyl-4'-Carboxylphenyl Acridine-9-Carboxylate

A mixture of 2',6'-dimethyl-4'-benzyloxycarbonylphenyl acridine-9-carboxylate from Example 4 (5.4 g, 11.7 mmole), 100 ml of glacial acetic acid, and 25 ml of 48% hydrogen bromide was heated at 100° C. for 3 hours and cooled. The reaction mixture was added to 600 ml of water and extracted with 20% methanol in chloroform (3 times with 100 ml). The organic extracts were combined evaporated, and the residue was washed with hexane on a funnel having a fritted disc. The yellow solid (obtained as a HBr salt) was suspended in chloroform and neutralized with a slight excess of triethylamine before being washed with water, dried over sodium sulfate, and evaporated (3.83 g. 88%). The desired product thus obtained had an Rf of 0.4 in 10% methanol/chloroform.

EXAMPLE 6

Preparation of
2',6'-Dimethyl-4'-(N-Succinimidyloxycarbonyl) Phenyl Acridine-9-Carboxylate A solution of 2',6'-dimethyl-4'-carboxylphenyl acridine-9-carboxylate from Example 5 (3.58 g, 9.64 mmole) in 450 ml of DMF was placed in a one liter round bottom flask equipped with a drying tube and a stirring bar. The solution was cooled in an ice bath for 10 minutes, then mixed with a solution of dicyclohexylcarbodiimide (3.0 g. 14.6 mmole) in 50 ml of DMF. The reaction mixture was stirred in an ice bath for 30 minutes, mixed with a solution of N-hydroxysuccinimide (1.7 g. 14.5 mmole) in 50 ml of DMF, stirred at room temperature overnight, and evaporated to dryness. The residue was extracted with 150 ml of methylene chloride, then filtered. The filtrate was concentrated to a wet solid, triturated with 20 ml of ethylacetate, filtered, and dried in a vacuum desiccator to obtain the crude product (3.5 g). Further purification of the product was carried out using conventional flash chromatography technique. The silica gel (J. T. Baker, #7024-1) column was packed and eluted with chloroform/ethylacetate (4:1, v/v). The fractions having an Rf of 0.28 on silica gel TLC plate when developed with ethyl ether/ethylacetate (4:1, v/v) were pooled and evaporated to give a white solid (95% pure by HPLC). Repeated flash chromatography purification using a packed silica gel column packed and eluted with hexane/acetone (2:1) yielded the pure desired product (34% yield, m.p. 276°-277° C.).

EXAMPLE 7

Preparation of
2',6'-Dimethyl-4'-(N-Succinimidyloxycarbonyl) Phenyl 10-Methyl-Acridinium-9-Carboxylate Methosulfate To a solution of 2',6'-dimethyl-4'-(N-succinimidyloxycarbonyl) phenyl acridine-9-carboxylate from Example 6 (91.5 mg. 0.195 mmole) in 3.8 ml of methylene chloride is added 2.0 ml of redistilled dimethyl sulfate. The resulting solution is refluxed for four days under anhydrous condition. To the yellow homogeneous solution at room temperature is added 15 ml of diethyl ether which precipitates the desired product. Purification is by means of recrystallization from methylene chloride and diethyl ether mixture to give a yellow solid, (92.7 mg, 80%) m.p. 228°-230° C.

EXAMPLE 8

Preparation of
2',6'-Dimethyl-4'-Benzyloxycarbonylphenyl 10-Methyl-Acridinium-9-Carboxylate Methosulfate A solution of 2',6'-dimethyl-4'-benzyloxycarbonylphenyl acridine-9-carboxylate from Example 4 (46 ml, 0.1 mmole) in 1 ml of chloroform and 0.3 ml of dimethyl sulfate (3.17 mmole) were placed in a 25 ml round bottom flask equipped with a Vigreaux distillation column and a stirring bar. The solution was heated at 105° C. for 10 minutes, and cooled. The reaction mixture was diluted with 2 ml of methylene chloride, then anhydrous ethyl ether was added to obtain maximal precipitation of the desired product. The mixture was filtered, washed with ethyl ether, and air dried to give a yellow solid (46 mg, 78%).

It should be noted that during synthesis the $R_{10}$ moiety can be either as defined above, or, more often, it can be a precursor which later requires transformation into the defined moiety. For example, the precursor may comprise protective groups linked to the defined moiety which are removed to yield the defined moiety. Such synthesis techniques are known to the art.

Preparation of Present Conjugates

Depending on which $R_{10}$ coupling moiety is selected, the ester label can be reacted directly with the specific binding partner or the ligand, either in an aqueous or an organic media. Again such coupling techniques are well known to the art.

Light Emitting Efficiency

Interestingly, whereas alone the preferred ortho-dimethyl substituted aryl acridinium compound has one third the light emitting efficiency of the prior unsubstituted compound, when it is coupled to an antibody to form a conjugate, the light emitting efficiency of the present conjugate is tripled, and thus, unexpectedly becomes as efficient as the prior art conjugates.

It is believed that the present conjugate has a higher specific activity than past ones because the substituted acridinium ester has a much greater stability in the alkaline buffer solutions necessary for coupling than the unsubstituted compound.

More particularly, the following assay was performed on both the present ortho-dimethyl ester and the prior unsubstituted compound.

A conjugate was prepared by coupling an anti-TSH antibody to the polysubstituted acridinium ester of Example 7 according to a conventional protein-coupling procedure, however any number of such known methods would be suitable.

The final antibody concentration was 0.8 ng/ml. Ten microliters of a 1 in 1200 aqueous dilution of the conjugate were flashed by injecting 0.3 ml of a first solution containing 0.1N $HNO_3$, 0.1% $H_2O_2$, and 0.2% of Arquad# surfactant, followed by a second solution of 0.3 ml of 0.1 N NaOH. Light emission was integrated for two seconds on a Berthold luminometer.

The above process was duplicated except for the substitution of the prior unsubstituted acridinium ester compound.

The light emitting efficiencies of a conjugation made with the present ortho-dimethyl ester were comparable or better than similar conjugates made with the prior unsubstituted ester:

TABLE I

| Conjugate | Total Counts |
| --- | --- |
| Unsubstituted Ester | 3,408,030 |
| Unsubstituted Ester | 3,110,990 |
| Ortho-dimethyl Ester | 3,913,690 |
| Ortho-dimethyl Ester | 3,467,030 |

Conjugate Stability

The above prior unsubstituted ester conjugate and the ortho-dimethyl ester conjugate were tested also for stability. The retention of luminescent activity was tested under various pHs (using citrate-phosphate buffers) and temperatures. Five milliliter aliquots of each of the above conjugates were placed into two sets of three different buffers (pH 5.0, 7.4, and 8.0), each containing 0.1% BSA. One set was kept at 4°-8° C. as a control, while the other was subjected to 37° C. for seven days. At three days and seven days, 25 microliters of each buffered sample were flashed as described above. The results were as follows:

TABLE 2

| | Relative Stability of Heat-Stressed Versus Non-Heat-Stressed Conjugates | |
|---|---|---|
| pH | 3 days at 37° C. | 7 days at 37° C. |
| 5.0 | 77%/91%* | 62%/77% |
| 7.4 | 66%/101% | 46%/92% |
| 8.0 | 45%/102% | 13%/106% |

*The relative activity of the prior unsubstituted ester is expressed first, followed by that of the present ortho-dimethyl ester second. Thus, in the noted case the present ortho-dimethyl ester has 91% relative activity, while the prior unsubstituted ester has 77% relative activity. All activities are related back to their 2-8° C. stability.

Signal-to-Noise Comparison

The above prior unsubstituted ester conjugate and the present ortho-dimethyl ester also were tested for signal-to-noise (S/N) ratios in an immunoassay. The assay worked as follows:

100 microliters of either of the above conjugates is incubated for two hours at room temperature with 200ul of a TSH standard (Ciba Corning Diagnostics Corp., Medfield, Mass.). Incubations were done separately with four standards containing either 0, 0.4, 1.0, or 100uIU/ml of TSH. A second incubation was then performed by adding 500u microliters of sheep anti-TSH, MAGIC® magnetic particle conjugate (also available from Ciba Corning Diagnostics Corp.) to the above mixture, then waiting for 30 minutes at room temperature. A wash was done first by magnetically separating the particles from the solution, decanting the solution, then adding 500 microliters of water, followed by another magnetic separation. The washed particles were resuspended in 100 microliters of a solution containing 0.1N $HNO_3$ and 0.1% of $H_2O_2$. Flashing and counting were done according to the above-described procedures. The results were tabulated using ratios of the counts with a TSH standard containing TSH versus the zero TSH standard.

TABLE 3

| | Standard | | |
|---|---|---|---|
| Conjugate | 0.4 uIU/ml | 1.0 uIU/ml | 100 uIU/ml |
| Unsubstituted Ester | 1.4 | 1.9 | 20.7 |
| Ortho-dimethyl Ester | 1.9 | 2.3 | 44.5 |

The comparison of results indicated the present conjugate had a means increase in its signal-to-noise ratio of 57% over prior conjugates.

It should be apparent to one having ordinary skill in the art that many variations are possible without departing from the spirit and scope of the invention.

We claim:
1. A luminescent polysubstituted aryl acridinium ester selected from the group having the following structure:

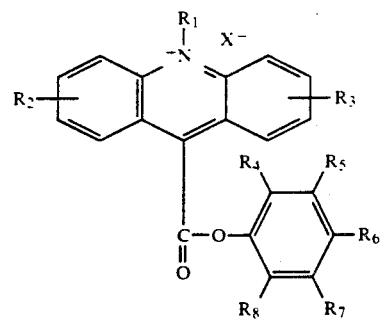

where $R_1$ is an alkyl, alkenyl, alkynyl, or aryl group; $R_2$, $R_3$, $R_5$, or $R_7$ are a hydrogen, amino, carboxyl, hydroxyl, alkoxyl, nitro, or halide group; $R_4$ or $R_8$ are an, alkoxyl, group; $R_6$ represents hydrogen or the following substituent:

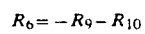

where $R_9$ is not required but if present is an alkyl, aryl, or aralkyl group, and $R_{10}$ is selected from the following:

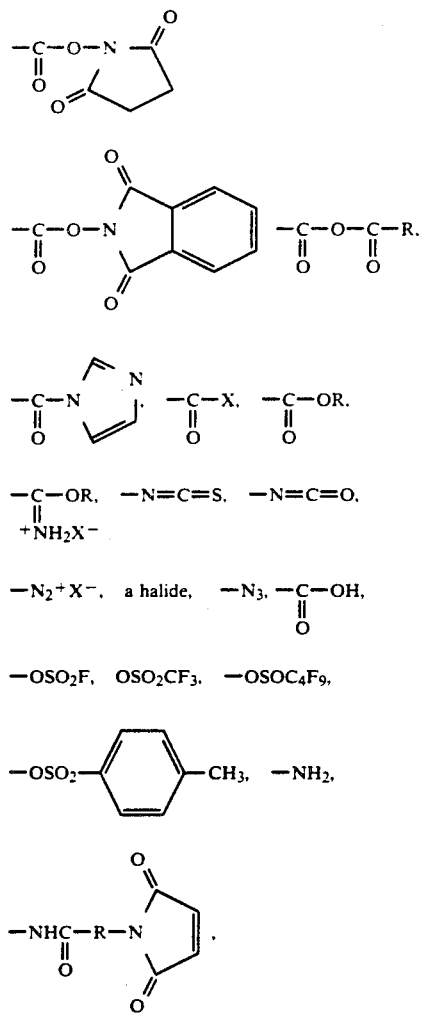

-continued

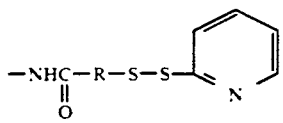

;X is $CH_3SO_4^-$, $OSO_2F^-$, a halide, $OSO_2CF_3^-$, $OSO_2C_4F_9^-$,

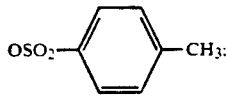

R is alkyl, aryl, aralkyl; and finally $R_5$, $R_6$, and $R_7$ substituent positions on the phenoxy ring are interchangeable.

2. A luminescent compound according to claim 1 wherein $R_1$ is a methyl group; $R_2$, $R_3$, $R_5$, and $R_7$ are hydrogen; $R_4$ and $R_8$ are a methoxyl group; $R_{10}$ is an N-succinimidyl oxycarbonyl group attached directly to the para-position of the phenoxy ring; and X is $CH_3SO_4^-$.

3. A luminescent polysubstituted aryl acridinium ester selected from the group having the following structure:

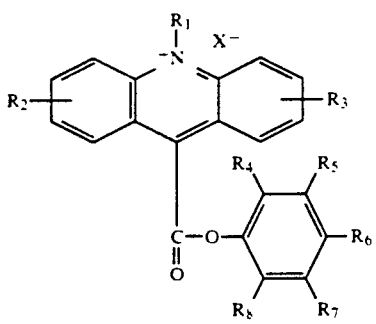

where $R_1$ is an alkyl, alkenyl, alkynyl, or aryl group; $R_2$, $R_3$, $R_5$, or $R_7$ are a hydrogen, amino, carboxyl, hydroxyl, alkoxyl, nitro, or halide group; $R_4$ or $R_8$ are an alkyl group; $R_6$ represents hydrogen; X is $CH_3SO_4^-$, $-OSO_2F$, a halide, $-OSO_2CF_3$, $-OSO_2C_4F_9$, or

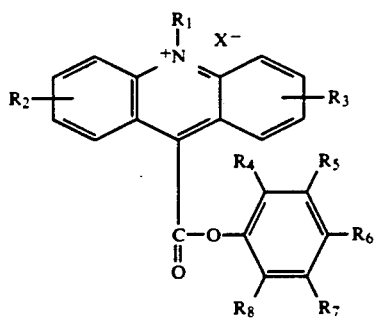

and the $R_5$, $R_6$ and $R_7$ substituent positions on the phenoxy ring are interchangeable.

4. A luminescent compound according to claim 3 wherein $R_1$ is a methyl group; $R_2$, $R_3$, $R_5$, and $R_7$ are hydrogen; and $R_4$ and $R_8$ are methyl group.

5. A luminescent polysubstituted aryl acridinium ester selected from the group having the following structure:

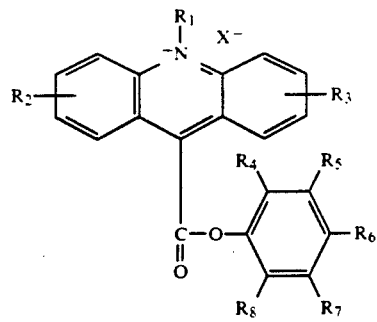

where $R_1$ is an alkyl, alkenyl, alkynyl, or aryl group; $R_2$, $R_3$, $R_5$, or $R_7$ are a hydrogen, amino, carboxyl, hydroxyl, alkoxyl, nitro, or halide group; $R_4$ or $R_8$ are an alkyl, alkenyl, alkynyl, aryl, alkoxyl, amino, amido, sulfonamido, or sulfide group; $R_6$ represents hydrogen or the following substituents:

$$R_6 = -R_9 - R_{10}$$

where $R_9$ is not required but optionally can be an alkyl, aryl, or aralkyl group, and $R_{10}$ is selected from the following:

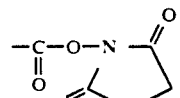

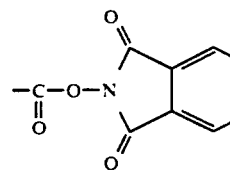 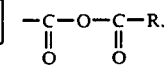

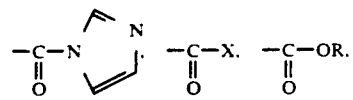

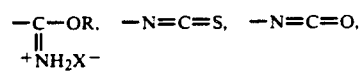

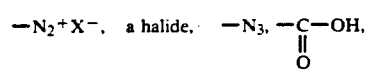

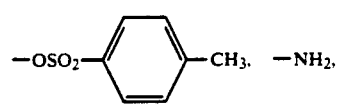

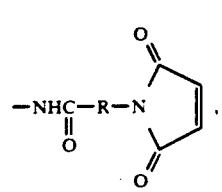

-continued

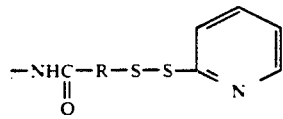

:X is $CH_3SO_4^-$, $OSO_2F^-$, a halide, $OSO_2CF_3^-$, $OSO_2C_4F_9^-$,

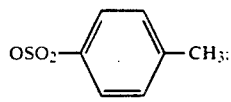

R is alkyl, aryl, aralkyl; and finally $R_5$, $R_6$, and $R_7$ substituent positions on the phenoxy ring are interchangeable.

6. A luminescent compound according to claim 5 wherein $R_1$ is a methyl group; $R_2$, $R_3$, $R_5$, and $R_7$ are hydrogen; $R_4$ and $R_8$ are a methyl group; $R_{10}$ is an N-succinimidyl oxycarbonyl group attached directly to the para-position of the phenoxy ring; and X is $CH_3SO_4^-$.

* * * * *